United States Patent

Klempau et al.

[11] Patent Number: 5,874,897
[45] Date of Patent: Feb. 23, 1999

[54] EMERGENCY-REPORTING SYSTEM FOR RESCUE OPERATIONS

[75] Inventors: Hans Jürgen Klempau, Bad Schwartau; Frank Rochlitzer, Altdorf, both of Germany

[73] Assignee: Drägerwerk AG, Lübeck, Germany

[21] Appl. No.: 773,971

[22] Filed: Dec. 26, 1996

[30] Foreign Application Priority Data

Apr. 10, 1996 [DE] Germany ................. 196 14 231.8

[51] Int. Cl.⁶ ................................... G08B 23/00
[52] U.S. Cl. ............... 340/573.1; 340/539; 340/825.36; 340/825.45; 340/825.49; 128/903; 128/904
[58] Field of Search ................. 340/573, 539, 340/825.36, 825.49, 825.45, 988; 128/903, 904, 630, 632, 633, 637, 667; 604/890.1, 891.1, 19

[56] References Cited

U.S. PATENT DOCUMENTS

| | | | |
|---|---|---|---|
| 4,531,527 | 7/1985 | Reinhold, Jr. et al. | 128/696 |
| 4,706,689 | 11/1987 | Man | 128/903 |
| 5,228,449 | 7/1993 | Christ et al. | 128/691 |
| 5,357,427 | 10/1994 | Langen et al. | 128/630 |
| 5,416,695 | 5/1995 | Stutman et al. | 128/630 |
| 5,474,574 | 12/1995 | Payne et al. | 607/7 |
| 5,534,974 | 7/1996 | Simms et al. | 340/990 |
| 5,544,651 | 8/1996 | Wilk | 128/633 |
| 5,626,630 | 5/1997 | Markowitz et al. | 607/60 |

FOREIGN PATENT DOCUMENTS 43 21 416 A1  1/1995  Germany.

*Primary Examiner*—Benjamin C. Lee
*Attorney, Agent, or Firm*—McGlew and Tuttle

[57] ABSTRACT

A personal emergency-reporting system for recognizing the site of an emergency with simultaneous warning of the nearest emergency physician/medical personnel. A portable patient data unit is provided which contains a satellite-supported global positioning system, which communicates with a patient data acquisition and evaluation unit via a computer and control unit, wherein the latter is connected to an emergency call transmitter. The transmitter sends patient data and the patient's position to an emergency call receiver in the case of an emergency. An automatic emergency-reporting system is provided by the present invention in order to make possible a rapid and specific rescue operation to a person whose health is acutely at risk.

17 Claims, 1 Drawing Sheet

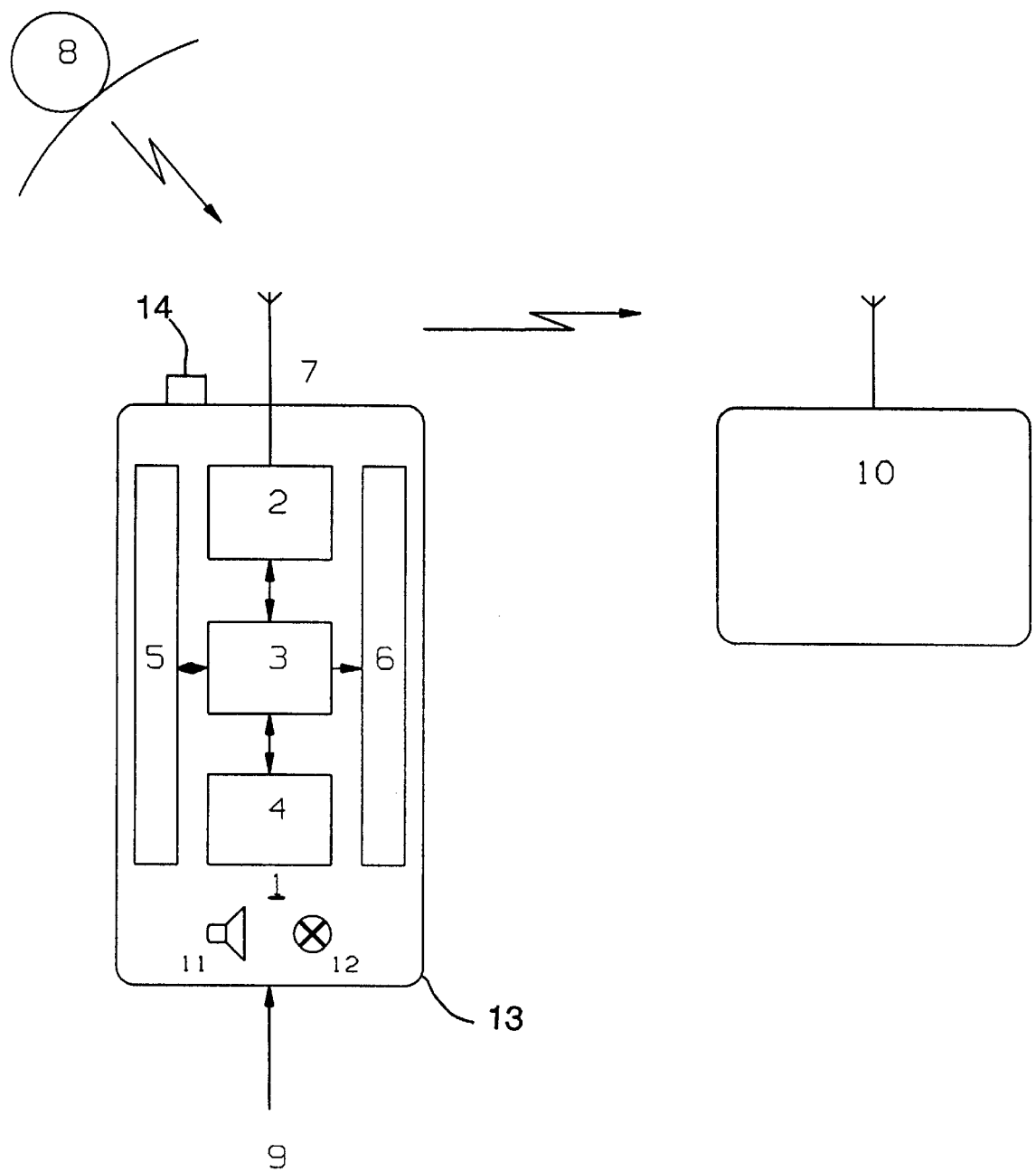

EMERGENCY-REPORTING SYSTEM FOR RESCUE OPERATIONS

FIELD OF THE INVENTION

The present invention pertains generally to emergency systems and more particularly to a personal emergency-reporting system.

BACKGROUND OF THE INVENTION

A vehicle emergency radio system, which comprises a positioning system, a crash sensor, and an emergency call transmitter as its essential elements, has been known from DE 43 21 416 A1. It is ensured with this system that an emergency call signal is sent by radio together with the instantaneously stored position data in the case of an accident, a rescue operation is possible after reception and forwarding to a rescue coordination center.

SUMMARY AND OBJECTS OF THE PRESENT INVENTION

The primary object of the present invention is to provide a personal, automatic emergency-reporting system, which makes possible a rapid, specific rescue operation to a person whose health is acutely at risk.

According to the invention, a personal emergency-reporting system is provided including a portable patient data unit which contains a satellite-supported Global Positioning System (GPS) receiver means. The GPS receiver means is connected to a patient data acquisition and evaluation unit via a computer and control unit. The computer and control unit are connected to an emergency call transmitter, which sends patient data and position information to an emergency call receiver in the case of an emergency.

The personal emergency-reporting system is preferably provided with the positioning system, the patient data acquisition and evaluation unit, the computer and control unit, and the emergency call transmitter arranged in a standard housing.

The patient data unit preferably has a reading and writing device for magnetic or optical data storage media, which is connected to the computer and control unit. The data storage medium with the patient data is preferably used to record the emergency operation for clinical treatment or for medical evaluation. The patient data unit preferably additionally has acoustic and/or optical signal transmitters, which are activated in the case of an emergency.

One essential advantage of the system according to the present invention is that the individual data of the patient in question, including personal history and dates of treatment, are stored in a suitable data storage medium during the accident and are thus available for recording the rescue operation, for the further treatment in the hospital, and for additional documentation and further evaluation purposes, e.g., the billing for services. In a preferred embodiment, the patient data unit, to be carried on the patients body, is arranged in a compact design in a standard housing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention are illustrated.

BRIEF DESCRIPTION OF THE DRAWINGS

In the drawings:

The only FIGURE is a schematic view that shows an exemplary embodiment according to the invention.

DESCRIPTION OF THE PREFERRED EMBODIMENT

Referring to the drawings in particular, the core of the system according to the present invention is a compact patient data unit 1, which can be carried by the patient, preferably directly on the body, and which preferably has the following functional elements in a standard, compact housing 13:

The satellite-supported Global Positioning System (GPS) 2 is in radio connection with a satellite 8 via an antenna 7 in order to determine the patient's exact position during the phase of operation of the patient data unit 1 after an emergency situation of the patient occurs.

The position data are polled by the computer and control unit 3 from the positioning system 2 as soon as an emergency of the patient has been determined on the basis of the current patient data determined by the patient data acquisition and evaluation unit 4. In another preferred embodiment of the present invention, the patient data unit 1 has an additional, acoustic and/or optical signal transmitter 11, 12, which warns the patient correspondingly when an emergency occurs. As an alternative or in addition, provisions may also be made for the patient to trigger an alarm via the computer and control unit 3 by actively actuating a switching element 14 of the patient data unit 1.

At any rate, via suitable sensors and patient data pickups 9, the patient data acquisition and evaluation unit 4 determines important medical parameters of the patient, e.g., the heart rate, blood pressure and additionally, depending on the patient's medical history, special additional parameters, such as cardiac arrhythmias, which may be of great significance for the occurrence of an emergency and the emergency operation itself, at predetermined time intervals. In addition, the patient data unit 1 has a data storage medium reading and writing device 5 to ensure the current storage and availability of all relevant data of the patient. The data storage medium is preferably an optical data storage medium of high storage capacity, which as an individual patient data file may contain both the patient's current status and his history as well as health insurance data. The data storage medium reading and writing device 5 communicates with the computer and storage unit 3. An emergency call is sent automatically if the computer and evaluation unit 3 now determines a change in the status of the patient that is relevant for the definition of an emergency by comparing stored, preset limit values with the current parameters of the patient, which are determined by means of sensors via patient data pickups 9.

The computer and control unit 3 sends a release signal in this case to the emergency call transmitter 6, which sends an emergency call signal by radio via the antenna 7 together with the patient's position data being polled instantaneously by the positioning system 2 and with patient data selected by the computer and control unit 3. The emergency radio signal with the position data and the selected patient data is received directly by the antenna of the nearest rescue coordination center/emergency call center 10. As an alternative, it would also be possible to use the nearest base station of a corresponding mobile radio telephone system.

By means of the position and patient data transmitted, a rapid and specific rescue operation is possible for the individual patient based on his personal indications, e.g., by the deployment of medical specialists and by providing special drugs and devices in the ambulance, emergency physician's car or rescue helicopter to be used.

After the site of the accidence has been reached, the data storage medium with the patient data can be removed from the patient data unit 1 and be introduced into a suitable, corresponding reading and writing unit in the rescue unit in order to record, document and evaluate the emergency treatment during the rescue operation as well as for the subsequent treatments in the hospital or during the rehabilitation. The data desired for the further use of the patient data unit 1 on the patient can subsequently be provided specifically on the data storage medium; these data may include, e.g., critical limit values for relevant parameters of the patient, so that the further use of the patient data unit 1 is thus made possible for an emergency operation by means of the individual patient data storage medium. The patient data unit 1 is preferably operated by rechargeable batteries as a self-contained unit.

While a specific embodiment of the invention has been shown and described in detail to illustrate the application of the principles of the invention, it will be understood that the invention may be embodied otherwise without departing from such principles.

What is claimed is:

1. A personal emergency-reporting system for a patient comprising in combination:

a portable patient data unit including a housing carriable by a body of the patient, a satellite-supported Global Positioning System receiver means, a computer and control unit, a patient data acquisition and evaluation unit connected to said Global Positioning System receiver means via said computer and control unit, an emergency call transmitter connected to said computer and control unit for transmitting patient data and positions in the case of an emergency; and an emergency call receiver, said receiver means, said patient data acquisition and evaluation unit, said computer and control unit, and said emergency call transmitter are arranged in said housing;

data storage means connected to said computer and control unit for recording said patient data when said emergency is present, said storage means also including personal history and previous treatment information of the patient, said storage means includes a reading and writing device for magnetic or optical data storage media which is connected to said computer and control unit and also includes means for being read and written to by a rescue unit and hospital equipment.

2. A personal emergency-reporting system in accordance with claim 1, wherein said data storage medium with the patient data is used to record the emergency event for later clinical treatment or medical evaluation.

3. A personal emergency-reporting system in accordance with claim 1, wherein said patient data unit additionally includes acoustic and/or optical signal transmitters, which are activated in the case of an emergency.

4. A process for personal emergency-reporting, the process comprising the steps of:

providing an individual with a portable patient data unit including a satellite-supported Global Positioning System receiver means, a computer and control unit, a patient data acquisition and evaluation unit connection to said Global Positioning System receiver means via said computer and control unit, and an emergency call transmitter connected to said computer and control unit for transmitting patient data and positions in the case of an emergency;

storing personal history and previous treatment information of the patient in a storage means;

monitoring patient parameters with said patient data acquisition and evaluation unit at predetermined time intervals;

recording said patient parameters in said storage means when said emergency is present;

determining if an emergency situation is occurring based on an evaluation of said patient parameters with said computer and control unit;

providing at least one emergency call receiver; and transmitting patient parameter data and patient position data from said potable patient data unit to said emergency call receiver upon said computer and control unit determining that an emergency situation is occurring;

reading and writing to said storage means by rescue and hospital equipment.

5. A personal emergency-reporting process in accordance with claim 4, wherein said patient data unit additionally includes acoustic and/or optical signal transmitters, which are activated in the case of an emergency.

6. A personal emergency-reporting process in accordance with claim 4, wherein a plurality of emergency call receivers are provided defining emergency call receiving cells distributed over a geographic region whereby the nearest cell receives the emergency call.

7. A personal emergency-reporting process in accordance with claim 4, wherein said receiver means, said patient data acquisition and evaluation unit, said computer and control unit, and said emergency call transmitter are arranged in a portable patient data unit housing.

8. A personal emergency-reporting process in accordance with claim 7, wherein said patient data unit has a reading and writing device for magnetic or optical data storage media, which is connected to said computer and control unit.

9. A personal emergency-reporting process in accordance with claim 4, wherein said patient data unit has a reading and writing device for magnetic or optical data storage media, which is connected to said computer and control unit.

10. A personal emergency-reporting process in accordance with claim 9, wherein said data storage medium with the patient data is used to record the emergency event for latter clinical treatment or medical evaluation.

11. A personal emergency-reporting system for a patient, the system comprising:

a portable patient data unit including a housing carriable on a body of the patient;

a satellite-supported Global Positioning System receiver means connected to said data unit and for receiving position data from a Global Positioning System;

a patient data acquisition and evaluation means positioned in said housing for determining medical parameters of the patient;

a computer and control unit positioned in said housing of said data unit, said computer and control unit being connected to said receiver means and said acquisition and evaluation means, said computer and control unit determining if an emergency situation is present based on said medical parameters;

an emergency call transmitter connected to said computer and control unit for receiving said medical parameters and said position data from said computer and control unit when said emergency situation is present, said transmitter transmitting an emergency signal when said emergency situation is present, said emergency signal including said medical parameters and said position data;

an emergency call receiver spaced from said data unit, said emergency call receiver receiving said emergency signal from said data unit, said emergency call receiver providing an indication of said emergency situation and providing said medical parameters and position data to a user of said emergency call receiver with said indication of said emergency situation;

a data storage means connected to said computer and control unit for recording said medical parameters when said emergency situation is present, said storage means also including personal history and previous treatment information of the patient, said storage means includes means for being read and written to by a rescue unit and hospital equipment.

12. A personal emergency-reporting system in accordance with claim 11, wherein said patient data unit has a reading and writing device for magnetic or optical data storage media, which is connected to said computer and control unit.

13. A personal emergency-reporting system in accordance with claim 11, wherein said patient data unit additionally includes acoustic and/or optical signal transmitters, which are activated in the case of an emergency.

14. A system in accordance with claim 11, wherein:

a personal emergency switch is connected to said housing for the patient to create an emergency situation;

said acquisition and evaluation means determines heart rate, blood pressure, and cardiac arrhythmias.

15. A personal emergency-reporting system in accordance with claim 11, wherein said receiver means, said patient data acquisition and evaluation unit, said computer and control unit, and said emergency call transmitter are arranged in said housing of said data unit.

16. A personal emergency-reporting system in accordance with claim 15, wherein said patient data has a reading and writing device for magnetic or optical data storage media, which is connected to said computer and control unit.

17. A personal emergency-reporting system in accordance with claim 16, wherein said data storage medium with the patient data is used to record the emergency event for later clinical treatment or medical evaluation.

* * * * *